US012778952B2

(12) United States Patent
Legeai-Mallet

(10) Patent No.: US 12,778,952 B2
(45) Date of Patent: Nov. 3, 2026

(54) INFIGRATINIB FOR TREATMENT OF FGFR3-RELATED SKELETAL DISEASES DURING PREGNANCY

(71) Applicants: INSERM (INSTITUT NATIONAL DE LA SANTÉ ET DE LA RECHERCHE MÉDICALE), Paris (FR); UNIVERSITÉ DE PARIS, Paris (FR); ASSISTANCE PUBLIQUE-HÔPITAUX DE PARIS (APHP), Paris (FR); FONDATION IMAGINE, Paris (FR)

(72) Inventor: Laurence Legeai-Mallet, Paris (FR)

(73) Assignees: INSERM (INSTITUT NATIONAL DE LA SANTÉ ET DE LA RECHERCHE MÉDICALE), Paris (FR); UNIVERSITÉ DE PARIS, Paris (FR); ASSISTANCE PUBLIQUE-HÔPITAUX DE PARIS (APHP), Paris (FR); FONDATION IMAGINE, Paris (FR)

( * ) Notice: Subject to any disclaimer, the term of this patent is extended or adjusted under 35 U.S.C. 154(b) by 0 days.

(21) Appl. No.: 18/589,498

(22) Filed: Feb. 28, 2024

(65) Prior Publication Data

US 2024/0285626 A1 Aug. 29, 2024

Related U.S. Application Data

(63) Continuation of application No. 17/280,620, filed as application No. PCT/EP2019/076241 on Sep. 27, 2019, now abandoned.

(30) Foreign Application Priority Data

Sep. 28, 2018 (EP) .................................... 18306275

(51) Int. Cl.
*A61K 31/506* (2006.01)
*A61P 19/00* (2006.01)

(52) U.S. Cl.
CPC ........... *A61K 31/506* (2013.01); *A61P 19/00* (2018.01)

(58) Field of Classification Search
CPC .............................. A61K 31/506; A61P 19/00
See application file for complete search history.

(56) References Cited

U.S. PATENT DOCUMENTS

| | | | | | |
|---|---|---|---|---|---|
| 9,931,341 | B2 * | 4/2018 | Legeai-Mallet | ...... B32B 27/302 | |
| 11,357,778 | B2 * | 6/2022 | Legeai-Mallet | ..... A61K 38/179 | |
| 2015/0011560 | A1 * | 1/2015 | Legeai-Mallet | ........... C08J 5/18 | 514/252.14 |
| 2016/0051549 | A1 * | 2/2016 | Legeai-Mallet | ........ A61P 19/00 | 514/252.2 |
| 2024/0350490 | A1 * | 10/2024 | Legeai-Mallet | ..... A61K 38/177 | |

OTHER PUBLICATIONS

M. Jin et. al. Hum Mol Genet. Dec. 15, 2012;21(26):5443-55. (Year: 2012).*
Matsushita et. al. J Neurosurg Pediatr. Jan. 2017;19(1):91-95. (Year: 2017).*
E. Doherty et al. 2007, Am J Med Genet Part A 143A:3204-3215. (Year: 2007).*

* cited by examiner

*Primary Examiner* — James H Alstrum-Acevedo
*Assistant Examiner* — Manahil Mirghani Ali Abdalhameed
(74) *Attorney, Agent, or Firm* — WCF IP

(57) ABSTRACT

FGFR3 gain-of-function mutations are responsible for a family of chondrodysplasias namely, achondroplasia (ACH) the most common form of dwarfism, a lethal form of dwarfism thanatophoric dysplasia (TD) as well as and hypochondroplasia. Recent data demonstrate that Infigratinib (NVP-BGJ398) corrects pathological hallmarks of ACH and support it as a potential therapeutic approach for FGFR3-related skeletal diseases. Now the inventors has investigated the feasibility to treat the defective growth of the skeleton during the pregnancy with the drug. They treated pregnant female Fgfr3$^{Neo/Y367C}$ mice with the drug (4 mg/kg) that was injected subcutaneously at day E14.5 continuing daily through day 1 (after birth). The data indicated that BGJ398 treatment during 5 days in pregnant mice successfully repressed skeletal anomalies that occurred during embryonic stages. Accordingly, the present invention relates to methods for treatment of FGFR3-related skeletal diseases during pregnancy with Infigratinib.

4 Claims, 3 Drawing Sheets

Figure 1A:
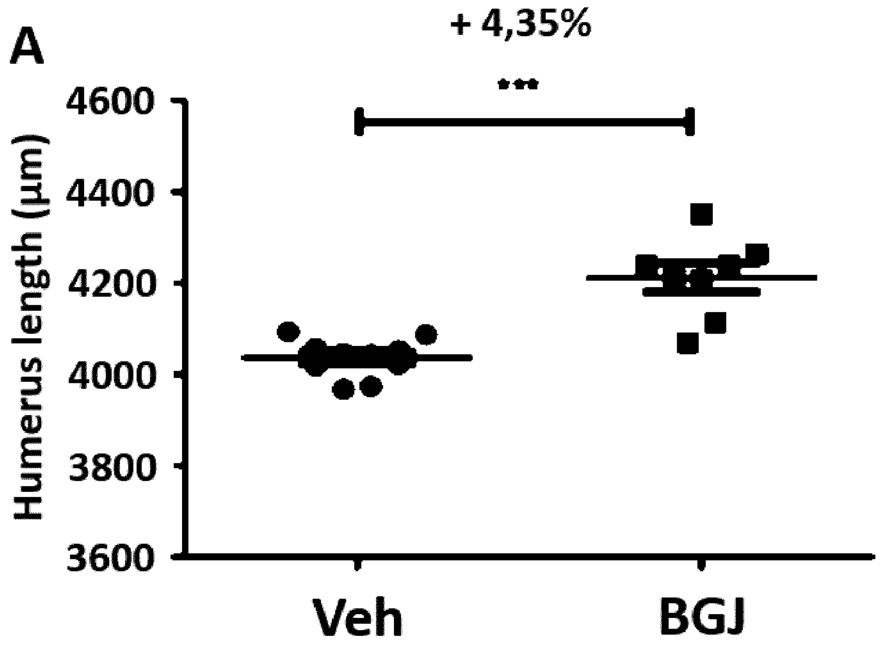

Specification includes a Sequence Listing.

INFIGRATINIB FOR TREATMENT OF FGFR3-RELATED SKELETAL DISEASES DURING PREGNANCY

FIELD OF THE INVENTION

The present invention relates to methods for treatment of FGFR3-related skeletal diseases during pregnancy.

REFERENCE TO SEQUENCE LISTING

A computer readable xml file entitled "13490080US2_seqlisting.xml", that was created on Feb. 27, 2024, with a file size of about 2,804 bytes, contains the sequence listing for this application, has been filed with this application, and is hereby incorporated by reference in its entirety.

BACKGROUND OF THE INVENTION

Fibroblast growth factor receptors (FGFRs) are a family of five receptor tyrosine kinases (RTKs) and are important regulators of skeleton development during endonchondral and membranous ossification throughout embryonic and postnatal development. FGFR3 is expressed in both bone and cartilage and FGFR3 signaling regulates a variety of biological events during skeletal development. FGFR3 gain-of-function mutations are responsible for a family of chondrodysplasias namely, *achondroplasia* (ACH) the most common form of dwarfism, a lethal form of dwarfism thanatophoric dysplasia (TD) as well as and hypochondroplasia (HCH). Pathogenic dominant FGFR3 mutations also cause craniosynostosis. Muenke syndrome is the most common craniosynostosis syndrome and Crouzon syndrome associated with acanthosis *nigricans* (CAN) is a rare syndrome. FGFR3 plays a significant role in growth plate cartilage, acting to inhibit both the rate of proliferation and the initiation of the chondrocyte hypertrophy. Recent data demonstrate that Infigratinib (NVP-BGJ398) corrects pathological hallmarks of ACH and support it as a potential therapeutic approach for FGFR3-related skeletal diseases (Komla-Ebri, D., Dambroise, E., Kramer, I., Benoist-Lasselin, C., Kaci, N., Le Gall, C. & Kneissel, M. (2016). *Tyrosine kinase inhibitor NVP-BGJ398 functionally improves FGFR3-related dwarfism in mouse model. The Journal of clinical investigation,* 126(5), 1871-1884 and Biosse Duplan, M., Komla-Ebri, D., Heuzé, Y., Estibals, V., Gaudas, E., Kaci, N. & Porta, D. G. (2016). *Meckel's and condylar cartilages anomalies in achondroplasia result in defective development and growth of the mandible. Human molecular genetics,* 25(14), 2997-3010).

SUMMARY OF THE INVENTION

The present invention relates to methods for treatment of FGFR3-related skeletal diseases during pregnancy. In particular, the present invention is defined by the claims.

DETAILED DESCRIPTION OF THE INVENTION

The present invention relates to a method of treating a FGFR3-related skeletal disease in a fetus comprising administering to the pregnant subject an effective amount of Infigratinib.

As used herein, the term "subject" denotes a mammal, such as a rodent, a feline, a canine, and a primate. Particularly, the subject according to the invention is a human. As used herein, the term "subject" encompasses "patient".

As used herein, the terms "FGFR3", "FGFR3 tyrosine kinase receptor" and "FGFR3 receptor" are used interchangeably throughout the specification and refer to all of the naturally-occurring isoforms of FGFR3. An exemplary human amino acid sequence of FGFR3 is represented by SEQ ID NO:1.

SEQ ID NO: 1

```
>sp|P22607|FGFR3_HUMAN Fibroblast growth
factor receptor 3 OS = Homo sapiens
OX = 9606 GN = FGFR3 PE = 1 SV = 1
MGAPACALALCVAVAIVAGASSESLGTEQR
VVGRAAEVPGPEPGQQEQLVFGSGDAVELS
CPPPGGGPMGPTVWVKDGTGLVPSERVLVG
PQRLQVLNASHEDSGAYSCRQRLTQRVLCH
FSVRVTDAPSSGDDEDGEDEAEDTGVDTGA
PYWTRPERMDKKLLAVPAANTVRFRCPAAG
NPTPSISWLKNGREFRGEHRIGGIKLRHQQ
WSLVMESVVPSDRGNYTCVVENKFGSIRQT
YTLDVLERSPHRPILQAGLPANQTAVLGSD
VEFHCKVYSDAQPHIQWLKHVEVNGSKVGP
DGTPYVTVLKTAGANTTDKELEVLSLHNVT
FEDAGEYTCLAGNSIGFSHHSAWLVVLPAE
EELVEADEAGSVYAGILSYGVGFFLFILVV
AAVTLCRLRSPPKKGLGSPTVHKISRFPLK
RQVSLESNASMSSNTPLVRIARLSSGEGPT
LANVSELELPADPKWELSRARLTLGKPLGE
GCFGQVVMAEAIGIDKDRAAKPVTVAVKML
KDDATDKDLSDLVSEMEMMKMIGKHKNIIN
LLGACTQGGPLYVLVEYAAKGNLREFLRAR
RPPGLDYSFDTCKPPEEQLTFKDLVSCAYQ
VARGMEYLASQKCIHRDLAARNVLVTEDNV
MKIADFGLARDVHNLDYYKKTTNGRLPVKW
MAPEALFDRVYTHQSDVWSFGVLLWEIFTL
GGSPYPGIPVEELFKLLKEGHRMDKPANCT
HDLYMIMRECWHAAPSQRPTFKQLVEDLDR
VLTVTSTDEYLDLSAPFEQYSPGGQDTPSS
SSSGDDSVFAHDLLPPAPPSSGGSRT
```

As used herein, the expressions "constitutively active FGFR3 receptor variant", "constitutively active mutant of the FGFR3" or "mutant FGFR3 displaying a constitutive activity" are used interchangeably and refer to a mutant of said receptor exhibiting a biological activity (i.e. triggering downstream signaling), and/or exhibiting a biological activity which is higher than the biological activity of the corresponding wild-type receptor in the presence of FGF ligand. A constitutively active FGFR3 variant according to the invention is in particular chosen from the group consisting of (residues are numbered according to their position in the precursor of fibroblast growth factor receptor 3 isoform 1-806 amino acids long-): a mutant wherein the serine residue at position 84 is substituted with lysine (named herein below S84L); a mutant wherein the arginine residue at position 248 is substituted with cysteine (named herein below R200C); a mutant wherein the arginine residue at position 248 is substituted with cysteine (named herein below R248C); a mutant wherein the serine residue at position 249 is substituted with cysteine (named herein below S249C); a mutant wherein the proline residue at position 250 is substituted with arginine (named herein below P250R); a mutant wherein the asparagine residue at position 262 is substituted with histidine (named herein below N262H); a mutant wherein the glycine residue at position 268 is substituted with cysteine (named herein below G268C); a mutant wherein the tyrosine residue at position 278 is substituted with cysteine (named herein below Y278C); a mutant wherein the serine residue at position 279 is substituted with cysteine (named herein below S279C); a mutant wherein the glycine residue at position 370 is substituted with cysteine (named herein below G370C); a mutant wherein the serine residue at position 371 is substituted with cysteine (named herein below S371C); a mutant wherein the tyrosine residue at position 373 is substituted with cysteine (named herein below Y373C); a mutant wherein the glycine residue at position 380 is substituted with arginine (named herein below G380R); a mutant wherein the valine residue at position 381 is substituted with glutamate (named herein below V381E); a mutant wherein the alanine residue at position 391 is substituted with glutamate (named herein below A391E); a mutant wherein the asparagine residue at position 540 is substituted with Lysine (named herein below N540K); a mutant wherein the termination codon is eliminated due to base substitutions, in particular the mutant wherein the termination codon is mutated in an arginine, cysteine, glycine, serine or tryptophane codon (named herein below X807R, X807C, X807G, X807S and X807W, respectively); a mutant wherein the lysine residue at position 650 is substituted with another residue, in particular with methionine, glutamate, asparagine or glutamine (named herein below K650M, K650E, K650N and K650Q). Typically, a constitutively active FGFR3 variant according to the invention is K650M, K650E or Y373C mutant.

As used herein, the term "FGFR3-related skeletal disease" is intended to mean a skeletal disease that is caused by an abnormal increased activation of FGFR3, in particular by expression of a constitutively active mutant of the FGFR3 receptor, in particular a constitutively active mutant of the FGFR3 receptor as described above. The term encompasses FGFR3-related chondrodysplasia and FGFR3-related craniosynostosis.

Examples of FGFR3-related chondrodysplasias include but are not limited to thanatophoric dysplasia type I, thanatophoric dysplasia type II, hypochondroplasia, *achondroplasia* and SADDAN (severe *achondroplasia* with developmental delay and acanthosis *nigricans*). In some embodiments, the FGFR3-related skeletal ostcochondrodysplasia is caused by expression in the subject of a constitutively active FGFR3 receptor variant such as defined above. In some embodiments, the FGFR3-related chondrodysplasia is an *achondroplasia* caused by expression of the G380R constitutively active mutant of the FGFR3 receptor. In some embodiments, the FGFR3-related chondrodysplasia is a hypochondroplasia caused by expression of the N540K, K650N, K650Q, S84L, R200C, N262H, G268C, Y278C, S279C, V381E, constitutively active mutant of the FGFR3 receptor. In some embodiments, the FGFR3-related chondrodysplasia is a thanatophoric dysplasia type I caused by expression of a constitutively active mutant of the FGFR3 receptor chosen from the group consisting of R248C, S248C, G370C, S371C; Y373C, X807R, X807C, X807G, X807S, X807W and K650M FGFR3 receptors. In some embodiments, the FGFR3-related chondrodysplasia is a thanatophoric dysplasia type II caused by expression of the K650E constitutively active mutant of the FGFR3 receptor. In some embodiments, the FGFR3-related chondrodysplasia is a severe achondroplasia with developmental delay and acanthosis nigricans caused by expression of the K650M constitutively active mutant of the FGFR3 receptor.

In some embodiments, the FGFR3-related craniosynostosis is Muenke syndrome caused by expression of the P250R constitutively active mutant of the FGFR3 receptor or Crouzon syndrome with acanthosis nigricans caused by expression of the A391E constitutively active mutant of the FGFR3 receptor.

Prenatal diagnosis of FGFR3-related skeletal diseases is routinely performed and typically includes ultrasound evaluation and confirmed by both genetic testing (i.e. DNA testing for mutations of FGFR3) using invasive diagnosis (e.g. amniocentesis or chorionic biopsy) or non-invasive prenatal diagnosis (NIPD) such as fetal DNA isolated from maternal blood.

As used herein, the term "treatment" or "treat" refer to both prophylactic or preventive treatment as well as curative, improving the patient's condition or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., daily, weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "Infigratinib" has its general meaning in the art and refers to 3-(2,6-dichloro-3,5-dimethoxyphenyl)-1-[6-[4-(4-ethylpiperazin-1-yl)anilino]pyrimidin-4-yl]-1-methylurea. The term is also known as NVP-BGJ398, BGJ398, or BGJ-398.

By a "therapeutically effective amount" of the Infigratinib as above described is meant a sufficient amount to provide a therapeutic effect. It will be understood, however, that the total daily usage of the Infigratinib will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the Infigratinib of the present invention is administered to the subject in the form of a pharmaceutical composition. Typically, the Infigratinib may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. In some embodiments, Infigratinib is orally or subcutaneously administered. For instance, suitable unit administration forms comprise oral-route forms such as tablets, gel capsules, powders, granules and oral suspensions or solutions, as well as sublingual and buccal administration forms. Infigratinib can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The invention will be further illustrated by the following figures and examples. However, these examples and figures should not be interpreted in any way as limiting the scope of the present invention.

FIGURES

FIG. 1: (A-C) the measures of the upper limbs (humerus (A), ulna (B), radius (C)) showed a significant improvement of the length with BGJ398.

FIG. 2: (A-B) the measures of the lower limbs (femur (A), tibia (B)) showed an improvement of the length with BGJ398.

EXAMPLE

Introduction

FGFR3-related chondrodysplasias encompass the most frequent chondrodysplasias (achondroplasia and hypochondroplasia) and Craniosynostoses (Muenke syndrome). All these osteochondrodysplasias are due to Fgfr3 germinal mutations, these Fgfr3 gain-of-function mutations impair the chondrogenesis and osteogenesis during the formation of the skeleton.

Objective of the Study

To demonstrate that it is feasible to treat with the BGJ398 the defective growth of the skeleton during the pregnancy.

Materials and Methods

The efficacy of BGJ398 treatment on skeletal development was demonstrated previously on Fgfr3$^{Y367C/+}$ pups exhibiting dwarfism (Komla-Ebri et al 2016, Biosse-Duplan et previously on Fgfr3Y367C/+al 2016).

We treated pregnant female Fgfr3$^{Neo/Y367C}$ mice that were mated with Cre$^{CMV/+}$ male mice (Pannier, S., Couloigner, V., Messaddeq, N., Elmaleh-Bergès, M., Munnich, A., Romand, R., & Legeai-Mallet, L. (2009). *Activating Fgfr*3 *Y*367*C. mutation causes hearing loss and inner ear defect in a mouse model of chondrodysplasia. Biochimica et Biophysica Acta* (*BBA*)*-Molecular Basis of Disease,* 1792(2), 140-147.). We injected BGJ398 (4 mg/kg) subcutaneously in 5 pregnant mice at day E14.5 continuing daily through day 1 (after birth). The pregnant mice received 5 injections of BGJ398 before delivery. We applied isofluorane inhalation to the pregnant mice during 20 seconds before the subcutaneous injections. All the pups were analyzed at day 1 after birth. At necropsy, all the long bones were measured and embedded in paraffin and were submitted to histology and immunology.

Results

The 5 females delivery 49 pups, 5 pups Fgfr3$^{Y367C/+}$ that received vehicle showed typical disease phenotype at birth, the 4 others Fgfr3$^{Y367C/+}$ that received BGJ398 showed improvement of the skeletal phenotype.

Figure 1B:
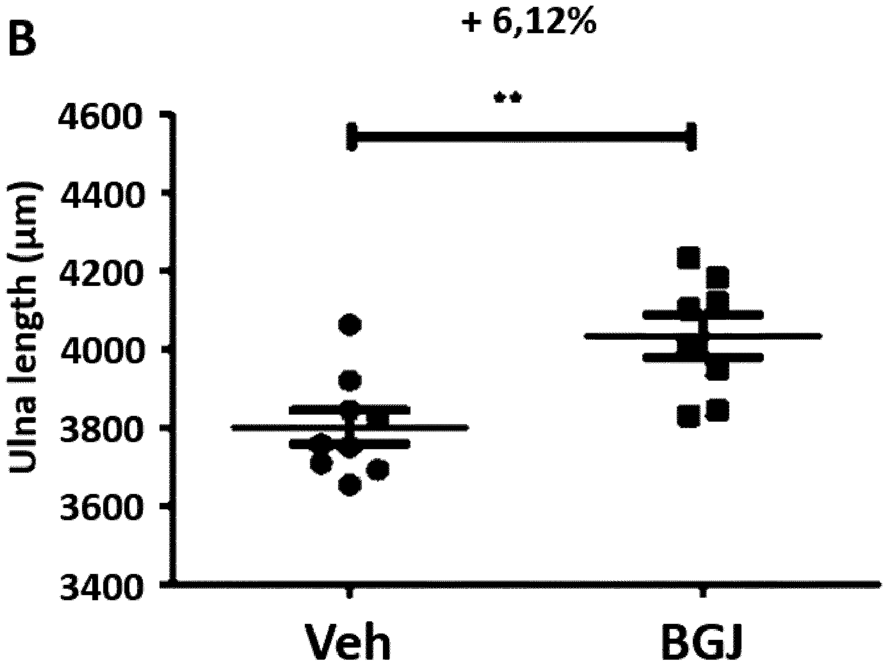
Figure 1C:
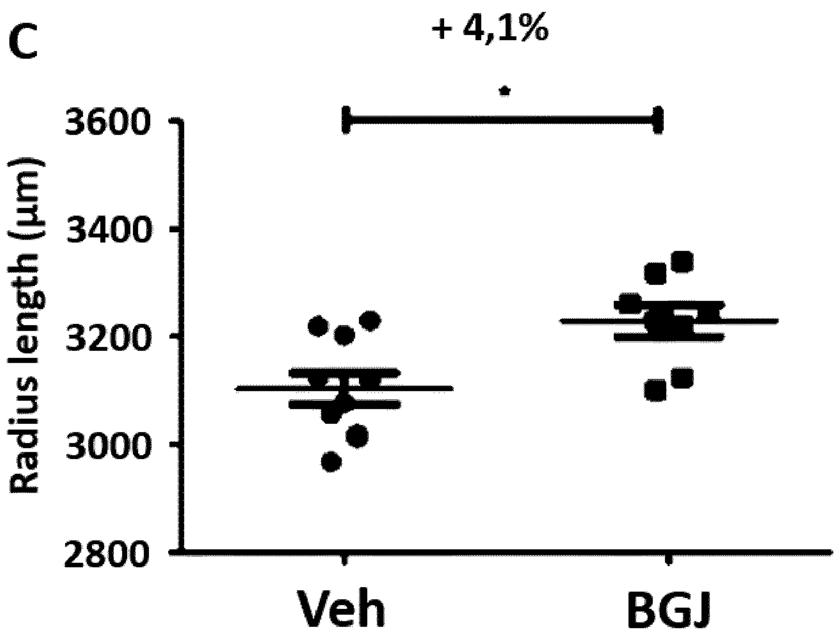

The measures of the upper limbs (humerus, ulna, radius) showed a significant improvement of the length (FIGS. 1A, 1B and 1C). We noted that the increase of the length of humerus, ulna, radius are +4.35%, +6.12%, 4, 1% respectively.

Figures 2A, 2B:
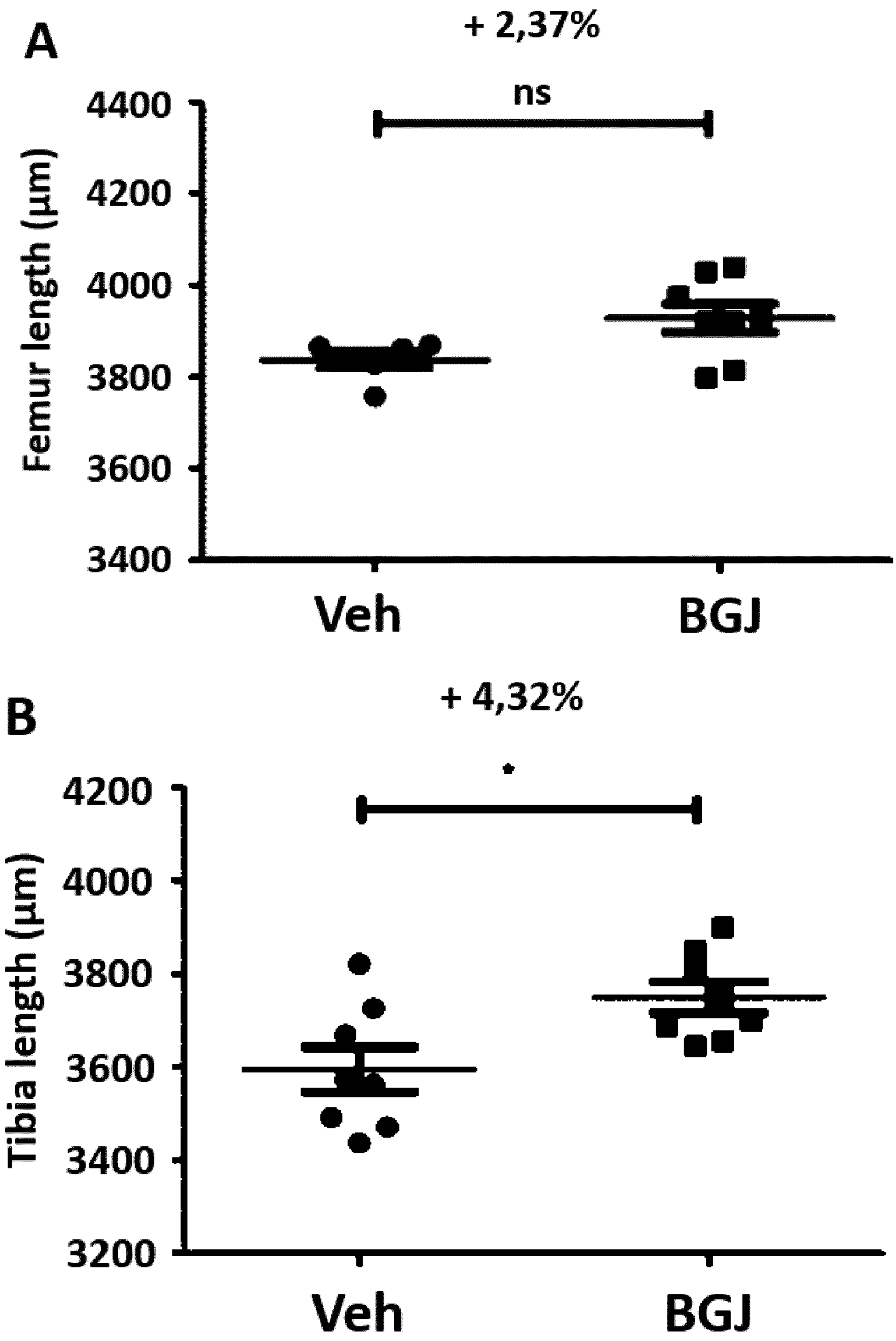

The measures of the lower limbs (femur, tibia) showed also an improvement of the size more obvious for the tibia (+4.32%) (FIGS. 2A and 2 B).

In order to confirm that BGJ398 treatment has modified the growth plate cartilage of the long bones, we performed histological analyses of the femurs. H&E staining showed that the chondrocytes are well organized in the proliferative zone in the treated growth plate cartilage compared to the controls (vehicle). In the hypertrophic zone, the size of the hypertrophic chondrocytes is increased in the cartilage treated with BGJ398 compared to cartilage treated with vehicle. These data confirm that BGJ398 has modified the growth plate cartilage (Data not shown).

CONCLUSIONS

The data indicated that BGJ398 treatment during 5 days in pregnant mice successfully repressed skeletal anomalies that occurred during embryonic stages. The treatment of the pregnant mice has permitted to cure earlier the skeletal pathology. The results suggest that BGJ398 cross the placenta at therapeutic level.

Treatment in human is feasible, because the diagnosis of FGFR3-related skeletal disorders will be done by genetic tests (familial case) or using ultrasound, it is possible to recognize fetal skeletal anomalies in the third trimester of pregnancy (neomutation).

REFERENCES

Throughout this application, various references describe the state of the art to which this invention pertains. The disclosures of these references are hereby incorporated by reference into the present disclosure.

The invention claimed is:

1. A method of treating a FGFR3-related skeletal disease in a fetus comprising administering to a pregnant subject an effective amount of Infigratinib, wherein the FGFR3-related skeletal disease is achondroplasia.

2. The method of claim 1 wherein Infigratinib is orally administered to the pregnant subject.

3. The method of claim 1 wherein Infigratinib is subcutaneously administered to the pregnant subject.

4. The method of claim 1 wherein said method increases the fetus limb length.

* * * * *

SEQUENCE LISTING

```
Sequence total quantity: 1
SEQ ID NO: 1            moltype = AA  length = 806
FEATURE                 Location/Qualifiers
source                  1..806
                        mol_type = protein
                        organism = Homo sapiens
SEQUENCE: 1
MGAPACALAL CVAVAIVAGA SSESLGTEQR VVGRAAEVPG PEPGQQEQLV FGSGDAVELS  60
CPPPGGGPMG PTVWVKDGTG LVPSERVLVG PQRLQVLNAS HEDSGAYSCR QRLTQRVLCH  120
FSVRVTDAPS SGDDEDGEDE AEDTGVDTGA PYWTRPERMD KKLLAVPAAN TVRFRCPAAG  180
NPTPSISWLK NGREFRGEHR IGGIKLRHQQ WSLVMESVVP SDRGNYTCVV ENKFGSIRQT  240
YTLDVLERSP HRPILQAGLP ANQTAVLGSD VEFHCKVYSD AQPHIQWLKH VEVNGSKVGP  300
DGTPYVTVLK TAGANTTDKE LEVLSLHNVT FEDAGEYTCL AGNSIGFSHH SAWLVVLPAE  360
EELVEADEAG SVYAGILSYG VGFFLFILVV AAVTLCRLRS PPKKGLGSPT VHKISRFPLK  420
RQVSLESNAS MSSNTPLVRI ARLSSGEGPT LANVSELELP ADPKWELSRA RLTLGKPLGE  480
GCFGQVVMAE AIGIDKDRAA KPVTVAVKML KDDATDKDLS DLVSEMEMMK MIGKHKNIIN  540
LLGACTQGGP LYVLVEYAAK GNLREFLRAR RPPGLDYSFD TCKPPEEQLT FKDLVSCAYQ  600
VARGMEYLAS QKCIHRDLAA RNVLVTEDNV MKIADFGLAR DVHNLDYYKK TTNGRLPVKW  660
MAPEALFDRV YTHQSDVWSF GVLLWEIFTL GGSPYPGIPV EELFKLLKEG HRMDKPANCT  720
HDLYMIMREC WHAAPSQRPT FKQLVEDLDR VLTVTSTDEY LDLSAPFEQY SPGGQDTPSS  780
SSSGDDSVFA HDLLPPAPPS SGGSRT                                     806
```